United States Patent
Hisler et al.

(10) Patent No.: US 11,286,221 B2
(45) Date of Patent: *Mar. 29, 2022

(54) METHOD FOR PRODUCING 1-CHLORO-3,3,3-TRIFLUOROPROPENE

(71) Applicant: Arkema France, Colombes (FR)

(72) Inventors: Kevin Hisler, Pierre-Benite (FR); Anne Pigamo, Pierre-Benite (FR); Laurent Wendlinger, Pierre-Benite (FR); Emmanuel Boussarie, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/251,328

(22) PCT Filed: Jun. 21, 2019

(86) PCT No.: PCT/FR2019/051520
§ 371 (c)(1),
(2) Date: Dec. 11, 2020

(87) PCT Pub. No.: WO2020/002800
PCT Pub. Date: Jan. 2, 2020

(65) Prior Publication Data
US 2021/0261485 A1    Aug. 26, 2021

(30) Foreign Application Priority Data

Jun. 27, 2018 (FR) ..................... 1855793

(51) Int. Cl.
*C07C 17/20* (2006.01)
*C07C 21/18* (2006.01)

(52) U.S. Cl.
CPC ............ *C07C 17/206* (2013.01); *C07C 21/18* (2013.01)

(58) Field of Classification Search
CPC .................................................. C07C 17/206
See application file for complete search history.

(56) References Cited

U.S. PATENT DOCUMENTS

| 2,583,812 A | 1/1952 | Briggs et al. |
| 2,882,243 A | 4/1959 | Milton |

(Continued)

FOREIGN PATENT DOCUMENTS

| CN | 101687735 A | 3/2010 |
| CN | 102216247 A | 10/2011 |

(Continued)

OTHER PUBLICATIONS

Ghanem, A. et al. "Static mixers: Mechanisms, applications,and characterization methods—A review" chemical engineering research and design 92 (2014) 205-228 (Year: 2014).*

(Continued)

*Primary Examiner* — Medhanit W Bahta
(74) *Attorney, Agent, or Firm* — Buchanan Ingersoll & Rooney P.C.

(57) ABSTRACT

The present invention relates to a process for producing 1-chloro-3,3,3-trifluoropropene (HCFO-1233zd), comprising: i) providing a stream A1 comprising HF, a stream A2 comprising 1,1,3,3-tetrachloropropene and/or 1,3,3,3-tetrachloropropene, and a reactor containing a liquid phase, ii) in said reactor, contacting, in said liquid phase, said stream A1 comprising HF with said stream A2 comprising 1,1,3,3-tetrachloropropene and/or 1,3,3,3-tetrachloropropene under conditions which are sufficient to produce a stream C comprising 1-chloro-3,3,3-trifluoropropene, HF and HCl, iii) recovering said stream C, characterized in that said reactor is provided with means for stirring said liquid phase so as to keep the temperature of said liquid phase substantially constant during step ii).

15 Claims, 4 Drawing Sheets

(56) References Cited

U.S. PATENT DOCUMENTS

| | | |
|---|---|---|
| 4,013,566 A | 3/1977 | Taylor |
| 5,616,819 A | 4/1997 | Boyce et al. |
| 5,684,219 A | 11/1997 | Boyce et al. |
| 5,705,779 A | 1/1998 | Demmin et al. |
| 5,877,359 A | 3/1999 | Elsheikh |
| 6,166,274 A | 12/2000 | Chen et al. |
| 6,403,847 B1 | 6/2002 | Nakada et al. |
| 8,404,907 B2 | 3/2013 | Nair et al. |
| 8,426,656 B2 | 4/2013 | Merkel et al. |
| 8,436,217 B2 | 5/2013 | Wang et al. |
| 8,704,017 B2 | 4/2014 | Pokrovski et al. |
| 8,877,990 B2 | 11/2014 | Fukuju et al. |
| 9,255,045 B2 | 2/2016 | Pigamo et al. |
| 9,643,903 B2 | 5/2017 | Pokrovski et al. |
| 9,834,499 B2 | 12/2017 | Pigamo et al. |
| 10,077,221 B2 | 9/2018 | Bonnet et al. |
| 10,227,275 B2 | 3/2019 | Pigamo et al. |
| 10,343,963 B2 | 7/2019 | Bonnet |
| 10,427,998 B2 | 10/2019 | Pigamo et al. |
| 10,532,965 B2 | 1/2020 | Pigamo et al. |
| 10,669,465 B2 | 6/2020 | Rached |
| 10,858,561 B2 | 12/2020 | Abbas et al. |
| 11,028,027 B2 | 6/2021 | Wendlinger et al. |
| 11,034,635 B2 | 6/2021 | Wendlinger et al. |
| 11,084,768 B2 | 8/2021 | Wendlinger et al. |
| 2001/0014707 A1 | 8/2001 | Thomas et al. |
| 2010/0191025 A1 | 7/2010 | Perdrieux |
| 2011/0196178 A1 | 8/2011 | Nyberg |
| 2011/0197602 A1 | 8/2011 | Abbas et al. |
| 2011/0201853 A1 | 8/2011 | Tung et al. |
| 2011/0218370 A1 | 9/2011 | Elsheikh et al. |
| 2011/0245549 A1 | 10/2011 | Merkel et al. |
| 2011/0259828 A1 | 10/2011 | Bouvier et al. |
| 2012/0059199 A1 | 3/2012 | Pokrovski et al. |
| 2012/0172636 A1 | 7/2012 | Pokrovski |
| 2012/0190902 A1 | 7/2012 | Nyberg |
| 2012/0226081 A1 | 9/2012 | Elsheikh et al. |
| 2012/0256119 A1 | 10/2012 | Bouvier et al. |
| 2012/0256120 A1 | 10/2012 | Bouvier et al. |
| 2012/0271070 A1 | 10/2012 | Wang et al. |
| 2012/0329893 A1 | 12/2012 | Abbas |
| 2013/0037058 A1 | 2/2013 | Abbas |
| 2013/0211154 A1 | 8/2013 | Cottrell et al. |
| 2013/0261353 A1 | 10/2013 | Pokrovski et al. |
| 2013/0261354 A1 | 10/2013 | Merkel et al. |
| 2014/0213831 A1 | 7/2014 | Nyberg |
| 2014/0221704 A1 | 8/2014 | Tung et al. |
| 2014/0264173 A1 | 9/2014 | Merkel et al. |
| 2015/0152235 A1 | 6/2015 | Abbas |
| 2015/0197467 A1 | 7/2015 | Pigamo et al. |
| 2016/0023974 A1 | 1/2016 | Bonnet et al. |
| 2016/0115104 A1 | 4/2016 | Pigamo et al. |
| 2016/0272561 A1 | 9/2016 | Rached et al. |
| 2017/0050904 A1 | 2/2017 | Ondrus |
| 2017/0081263 A1 | 3/2017 | Klausmeyer et al. |
| 2017/0174965 A1 | 6/2017 | Tsuchiya et al. |
| 2017/0210686 A1 | 7/2017 | Pigamo et al. |
| 2018/0015407 A1 | 1/2018 | Vittenet et al. |
| 2018/0093934 A1 | 4/2018 | Pigamo et al. |
| 2018/0148394 A1 | 5/2018 | Pigamo et al. |
| 2018/0346396 A1 | 12/2018 | Pigamo et al. |
| 2018/0354875 A1 | 12/2018 | Bonnet |
| 2019/0048241 A1 | 2/2019 | Abbas et al. |
| 2019/0152883 A1 | 5/2019 | Pigamo et al. |
| 2019/0276721 A1 | 9/2019 | Rached |
| 2019/0375698 A1 | 12/2019 | Pigamo et al. |
| 2020/0407293 A1 | 12/2020 | Wendlinger et al. |
| 2021/0002188 A1 | 1/2021 | Wendlinger et al. |
| 2021/0002189 A1 | 1/2021 | Wendlinger et al. |
| 2021/0238112 A1 | 8/2021 | Pigamo et al. |

FOREIGN PATENT DOCUMENTS

| | | |
|---|---|---|
| EP | 0 940 382 A1 | 9/1999 |
| EP | 1 566 600 A1 | 8/2005 |
| EP | 2 035 117 A | 3/2009 |
| FR | 1 257 034 | 1/1960 |
| FR | 2768727 A1 | 3/1999 |
| FR | 2 973 717 A1 | 10/2012 |
| FR | 2 973 809 A1 | 10/2012 |
| FR | 3 032 131 A1 | 8/2016 |
| FR | 3 041 632 A1 | 3/2017 |
| JP | 2000-95714 A | 4/2000 |
| JP | 2012-509324 A | 4/2012 |
| WO | WO 01/81353 A1 | 11/2001 |
| WO | WO 2008/127940 A1 | 10/2008 |
| WO | WO 2008/149011 A2 | 12/2008 |
| WO | WO 2008/149011 A3 | 12/2008 |
| WO | WO 2010/059496 A1 | 5/2010 |
| WO | WO 2010/063975 A1 | 6/2010 |
| WO | WO 2010/111067 A1 | 9/2010 |
| WO | WO 2012/067980 A2 | 5/2012 |
| WO | WO 2014/116562 A1 | 7/2014 |
| WO | WO 2015/175791 A1 | 11/2015 |
| WO | WO 2016/146940 A1 | 9/2016 |
| WO | WO 2017/031046 A1 | 2/2017 |

OTHER PUBLICATIONS

International Search Report (PCT/ISA/210) and translation and Written Opinion (PCT/ISA/237) dated Oct. 8, 219, by the European Patent Office as the International Searching Authority for International Application No. PCT/FR2019/051520.

Test No. 102: Melting point/Melting range, OECD guidelines for the testing of chemical products, Section 1, OECD Editions, Paris, 1995, available at http://dx.doi.org/10.1787/9789264069534-fr (with English translation) (17 pages).

Breck, Donald W., et al., "Zeolite Molecular Sieves", John Wiley & Sons Eds, (1974), 159 pages.

Boutier, Jean-Christophe, et al., U.S. Appl. No. 17/280,547 entitled "Stabilization of 1-Chloro-3,3,3-Trifluoropropene," filed in the U.S. Patent and Trademark Office filed Mar. 26, 2021.

\* cited by examiner

METHOD FOR PRODUCING
1-CHLORO-3,3,3-TRIFLUOROPROPENE

TECHNICAL FIELD OF THE INVENTION

The present invention relates to the production of hydrochlorofluoroolefins. More particularly, the present invention relates to the production of 1-chloro-3,3,3-trifluoropropene.

TECHNOLOGICAL BACKGROUND OF THE INVENTION 3,3,3-Trifluoro-1-chloropropene, or alternatively 1-chloro-3,3,3-trifluoropropene (HCFO-1233zd), exists in the form of two isomers: the cis isomer, namely Z-3,3,3-trifluoro-1-chloropropene (HCFO-1233zdZ), and the trans isomer, namely E-3,3,3-trifluoro-1-chloropropene (HCFO-1233zdE). They have different boiling points of, respectively, 18.5° C. for the trans compound and 39.5° C. for the cis compound.

Fluids based on E-3,3,3-trifluoro-1-chloropropene (HCFO-1233zdE) have found numerous applications in varied industrial fields, in particular as heat transfer fluids, propellants, foaming agents, blowing agents, gaseous dielectrics, monomers or polymerization media, support fluids, abrasive agents, drying agents, and fluids for energy production units.

The manufacture of HCFO-1233zdE is accompanied by a multitude of byproducts having a boiling point close to HCFO-1233zdE. This results in purification steps which are relatively complex and costly. The difficulties encountered during the purification of HCFO-1233zdE generally entail an appreciable loss of target product. In addition, the byproducts may form azeotropic compositions with the HCFO-1233zdE, making separation by simple distillation very difficult, or even impossible.

U.S. Pat. No. 5,877,359 discloses a process for preparing HCFO-1233zdE from 1,1,3,3-tetrachloropropene in liquid phase and in the absence of catalyst. The molar HF/1230za ratio in the fluorination reactor is from 12 to 500. U.S. Pat. No. 9,643,903 also discloses a process for fluorinating 1,1,3,3-tetrachloropropene in liquid phase and in the absence of catalyst, in an HF-rich medium.

Furthermore, a not inconsiderable amount of overfluorinated byproducts are observed, linked to the presence of this HF in large amount. The presence of 245fa may bring about a loss of yield, it being known that this mixture forms an azeotropic mixture with the primary product, 1233zdE (see in particular US2017/174965). It will therefore be difficult to separate and will have to be removed in the form of an azeotropic mixture, thus bringing about a loss of yield. There is therefore a need for new processes which minimize the drawbacks described above.

SUMMARY OF THE INVENTION

The present invention relates to a process for producing 1-chloro-3,3,3-trifluoropropene (HCFO-1233zd) comprising the steps of:
i) providing:
  a stream A1 comprising HF,
  a stream A2 comprising 1,1,3,3-tetrachloropropene and/or 1,3,3,3-tetrachloropropene, and
  a reactor containing a liquid phase,
ii) in said reactor, contacting, in said liquid phase, said stream A1 comprising HF with said stream A2 comprising 1,1,3,3-tetrachloropropene and/or 1,3,3,3-tetrachloropropene under conditions which are sufficient to produce a stream C comprising 1-chloro-3,3,3-trifluoropropene, HF and HCl,
iii) recovering said stream C,
characterized in that said reactor is provided with means for stirring said liquid phase so as to keep the temperature of said liquid phase substantially constant during step ii). The stirring means enables/enable good contact between the two immiscible starting materials, i.e. HF and 1,1,3,3-tetrachloropropene and/or 1,3,3,3-tetrachloropropene. The presence of stirring means makes it possible to prevent settling phenomena which could disturb the reaction process. It has been discovered that, when the temperature of the liquid phase is constant or substantially constant between the surface of the liquid volume and the bottom of the reactor during the reaction process, said liquid phase and the two starting materials exhibit very good homogeneity, which makes it possible to limit the formation of coproducts.

The present process makes it possible, by means of controlling the temperature of the liquid phase, to produce 1-chloro-3,3,3-trifluoropropene while at the same time minimizing the formation of overfluorinated coproducts or of heavy compounds (dimers or trimers of C3 compounds).

According to a preferred embodiment, during the implementation of step ii), the temperature of said liquid phase varies by a maximum of 2° C.

According to a preferred embodiment, said stirring means comprise a static mixer, a device for injecting an inert gas into said liquid phase, a device for recirculating the liquid phase, or a device for returning a flow of HF into said liquid phase, or a combination of two or more of these stirring means.

According to a preferred embodiment, the stirring means comprises a static mixer and the process comprises the steps of:
i) providing:
  a stream A1 comprising HF,
  a stream A2 comprising 1,1,3,3-tetrachloropropene and/or 1,3,3,3-tetrachloropropene, and
  a reactor containing a liquid phase and comprising a static mixer,
i') contacting said stream A1 with said stream A2 in said static mixer to form a mixture B comprising HF, 1,1,3,3-tetrachloropropene and/or 1,3,3,3-tetrachloropropene,
ii') diffusing said mixture B into said liquid phase in order to carry out step ii) proceeding from this.

According to one embodiment, said stream A1 and said stream A2 are preheated before carrying out step i') or ii).

According to a preferred embodiment, step ii) is carried out at a temperature of between 20° C. and 150° C.

According to a preferred embodiment, step ii) is carried out at a pressure of between 1 and 20 bara.

According to a preferred embodiment, the process is carried out in continuous mode in a single reactor.

According to a preferred embodiment, step ii) is carried out in the absence of catalyst.

According to a preferred embodiment, stream C is purified, preferably by distillation, to form a stream C1 comprising HCl and a stream C2 comprising 1-chloro-3,3,3-trifluoropropene and HF, said stream C2 itself being separated into a stream C3 comprising 1-chloro-3,3,3-trifluoropropene and a stream C4 predominantly comprising the HF recycled to step i') or ii).

According to a preferred embodiment, said liquid phase is low in HF, advantageously said liquid phase comprises less than 15% by weight of HF, preferably less than 10% by weight of HF, more preferentially less than 8% by weight of HF.

According to a preferred embodiment, stream C is a gaseous stream.

DETAILED DESCRIPTION OF THE INVENTION

Figure 1:
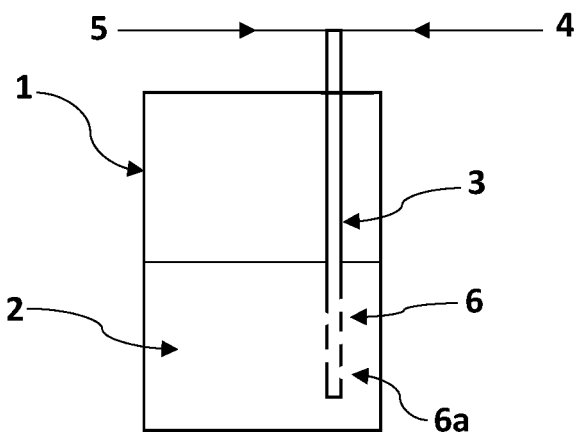
FIG. 1 schematically represents a reactor comprising, as stirring means, a static mixer, according to one embodiment of the present invention.

According to a first aspect of the present invention, a process for producing 1-chloro-3,3,3-trifluoropropene (HCFO-1233zd) is provided. The present process comprises the steps of:
  i) providing:
    a stream A1 comprising HF,
    a stream A2 comprising 1,1,3,3-tetrachloropropene and/or 1,3,3,3-tetrachloropropene, and
    a reactor containing a liquid phase,
  ii) in said reactor, contacting, in said liquid phase, said stream A1 comprising HF with said stream A2 comprising 1,1,3,3-tetrachloropropene and/or 1,3,3,3-tetrachloropropene under conditions which are sufficient to produce a stream C comprising 1-chloro-3,3,3-trifluoropropene, HF and HCl,
  iii) recovering said stream C.

Preferably, step ii) is carried out in a reactor provided with means for stirring said liquid phase. Said stirring means are suitable for keeping the temperature of said liquid phase substantially constant during step ii). The present process makes it possible, by means of controlling the temperature of the liquid phase, to produce 1-chloro-3,3,3-trifluoropropene while at the same time minimizing the formation of overfluorinated coproducts or of heavy compounds (dimers or trimers of C3 compounds).

The term "substantially constant" refers to a temperature which varies by a maximum of 3° C. in terms of absolute value, advantageously a maximum of 2.5° C. in terms of absolute value, preferably a maximum of 2° C. in terms of absolute value, more preferentially by a maximum of 1.5° C. in terms of absolute value, in particular by at most 1° C. in terms of absolute value, more particularly by at most 0.5° C. in terms of absolute value.

Thus, according to a preferred embodiment, during the implementation of step ii), the temperature of said liquid phase varies by a maximum of 3° C. in terms of absolute value, advantageously a maximum of 2.5° C. in terms of absolute value, preferably a maximum of 2° C. in terms of absolute value, more preferentially by a maximum of 1.5° C. in terms of absolute value, in particular by at most 1° C. in terms of absolute value, more particularly by at most 0.5° C. in terms of absolute value.

The temperature of said liquid phase is measured at several points within said phase in accordance with the methods known to those skilled in the art.

According to one particular embodiment, said low-HF liquid phase is a liquid phase comprising less than 15% by weight of HF, advantageously less than 10% by weight of HF, preferably less than 8% by weight of HF, more preferentially less than 6% by weight of HF, in particular less than 5% by weight of HF, more particularly less than 4% by weight of HF, favorably less than 2% by weight of HF, based on the total weight of said liquid phase.

According to an alternative embodiment, said liquid phase is rich in HF. Advantageously, in this alternative embodiment, said liquid phase comprises at least 25% by weight of HF, preferably at least 30% by weight of HF, more preferentially at least 35% by weight of HF. Thus, said liquid phase may comprise at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49% or at least 50% by weight of HF.

The embodiment in which said liquid phase is poor in HF is nevertheless favored.

Said liquid phase may comprise at least 10% by weight of compounds of formula (I) $C_3H_nF_mCl_p$ (I) in which n is an integer from 0 to 8, m is an integer from 0 to 8, and p is an integer from 0 to 8; preferably, n is an integer from 0 to 8, m is an integer from 0 to 6, and p is an integer from 0 to 6. Compounds of formula (I) may, for example, be $C_3Cl_6$, $C_3H_4Cl_4$ or $C_3H_3Cl_5$. Said liquid phase may preferably comprise at least 10% by weight of compounds of formula (I) $C_3H_nF_mCl_p$ (I) in which n is an integer from 1 to 8, m is an integer from 0 to 4, and p is an integer from 0 to 4; preferably, n is an integer from 1 to 4, m is an integer from 0 to 3, and p is an integer from 2 to 4. The compounds of formula (I) may be propane- or propene-type compounds comprising one or more chlorine atoms and/or one or more fluorine atoms. Said liquid phase may preferably comprise at least 10% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. More particularly, said liquid phase may comprise at least 10% by weight of compounds of formula (I) selected from the group consisting of $C_3H_2Cl_4$, $C_3H_2Cl_3F$, and $C_3H_2Cl_2F_2$. Said liquid phase may comprise at least 15% by weight of compounds of formula (I) $C_3H_nF_mCl_p$ (I) in which n is an integer from 0 to 8, m is an integer from 0 to 8, and p is an integer from 0 to 8; preferably, n is an integer from 0 to 8, m is an integer from 0 to 6, and p is an integer from 0 to 6. Said liquid phase may in particular comprise at least 15% by weight of compounds of formula (I) $C_3H_nF_mCl_p$ (I) in which n is an integer from 1 to 8, m is an integer from 0 to 4, and p is an integer from 0 to 4; preferably, n is an integer from 1 to 4, m is an integer from 0 to 3, and p is an integer from 2 to 4. Said liquid phase may preferably comprise at least 15% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. In particular, said liquid phase may comprise at least 15% by weight of compounds of formula (I) selected from the group consisting of $C_3H_2Cl_4$, $C_3H_2Cl_3F$, and $C_3H_2Cl_2F_2$. Said liquid phase may comprise at least 20%, at least 30%, at least 40%, at least 50%, at least 60%, at least 70%, at least 80% or at least 90% by weight of compounds of formula (I) $C_3H_nF_mCl_p$ (I) in which n is an integer from 0 to 8, m is an integer from 0 to 8, and p is an integer from 0 to 8; preferably, n is an integer from 0 to 8, m is an integer from 0 to 6, and p is an integer from 0 to 6. Said liquid phase may comprise at least 20%, at least 30%, at least 40%, at least 50%, at least 60%, at least 70%, at least 80% or at least 90% by weight of compounds of formula (I) $C_3H_nF_mCl_p$ (I) in which n is an integer from 1 to 8, m is an integer from 0 to 4, and p is an integer from 0 to 4; preferably, n is an integer from 1 to 4, m is an integer from 0 to 3, and p is an integer from 2 to 4. Said liquid phase may preferably comprise at least 20%, at least 30%, at least 40%, at least 50%, at least 60%, at least 70%, at least 80% or at least 90% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. In particular, said liquid phase may comprise at least 20%, at least 30%, at least 40%, at least 50%, at least 60%, at least 70%, at least 80% or at least 90% by weight of compounds of formula (I) selected from the group consisting of $C_3H_2Cl_4$, $C_3H_2Cl_3F$, and $C_3H_2Cl_2F_2$.

Preferably, said stream A2 comprises at least 10% by weight of 1,1,3,3-tetrachloropropene and/or 1,3,3,3-tetrachloropropene, based on the total weight of said stream A2. Advantageously, said stream A2 comprises at least 15% by weight of 1,1,3,3-tetrachloropropene and/or 1,3,3,3-tetrachloropropene, preferably at least 20% by weight of 1,1,3,3-tetrachloropropene and/or 1,3,3,3-tetrachloropropene, more preferentially at least 25% by weight of 1,1,3,3-tetrachloropropene and/or 1,3,3,3-tetrachloropropene, in particular at least 30% by weight of 1,1,3,3-tetrachloropropene and/or 1,3,3,3-tetrachloropropene, more particularly at least 35% by weight of 1,1,3,3-tetrachloropropene and/or 1,3,3,3-tetrachloropropene, favorably at least 40% by weight of 1,1,3,3-tetrachloropropene and/or 1,3,3,3-tetrachloropropene, advantageously favorably at least 45% by weight of 1,1,3,3-tetrachloropropene and/or 1,3,3,3-tetrachloropropene, preferentially favorably at least 50% by weight of 1,1,3,3-tetrachloropropene and/or 1,3,3,3-tetrachloropropene, and particularly favorably at least 55% by weight of 1,1,3,3-tetrachloropropene and/or 1,3,3,3-tetrachloropropene, based on the total weight of said stream A2.

Preferably, said stream A2 comprises at least 60% by weight or at least 65% by weight or at least 70% by weight or at least 75% by weight or at least 80% by weight or at least 85% by weight or at least 90% by weight or at least 95% by weight or at least 99% by weight of 1,1,3,3-tetrachloropropene and/or 1,3,3,3-tetrachloropropene, based on the total weight of said stream A2.

According to one embodiment, said stream A1 and said stream A2 are preheated before carrying out step i') or ii).

According to a preferred embodiment, step ii) is carried out at a temperature of between 20° C. and 150° C., advantageously between 50° C. and 150° C., preferably between 80 and 120° C. and in particular between 90 and 110° C.

According to a preferred embodiment, step ii) is carried out at a pressure of between 1 and 20 bara, advantageously between 5 and 20 bara, preferably between 5 and 18 bara, more preferentially between 7 and 18 bara, in particular between 10 and 18 bara, more particularly between 12 and 18 bara, favorably between 12 and 15 bara.

According to a preferred embodiment, the process is carried out in continuous mode in a single reactor.

According to a preferred embodiment, step ii) is carried out in the absence of catalyst. Alternatively, step ii) may be carried out in the presence of a catalyst. The catalyst may be selected from the group consisting of $TiCl_4$, $SnCl_4$, $TaCl_5$, $SbCl_3$, $AlCl_3$, $SbCl_5$, and a mixture of these. The catalyst may be partially or totally fluorinated. Preferably, the implementation of step ii) in the absence of catalyst is favored in order to avoid problems of corrosion of the reactor.

According to a preferred embodiment, said stirring means comprise a static mixer, a device for injecting an inert gas into said liquid phase, a device for recirculating the liquid phase, a mechanical stirring device, or a device for returning a flow of HF into said liquid phase, or a combination of two or more of these stirring means. Preferably, said stirring means comprise a static mixer, a device for injecting an inert gas into said liquid phase, a device for recirculating the liquid phase, or a device for returning a flow of HF into said liquid phase, or a combination of two or more of these means.

FIG. 1 schematically represents a reactor 1 comprising, as stirring means, a static mixer. In FIG. 1, the reactor 1 comprises a liquid phase 2 which is low in HF, as defined in the present application. The HF and the HCO-1230za are introduced into the reactor via a respective supply line 4 or 5. The HF and the HCO-1230za are mixed in the static mixer 3 feeding a diffusion device 6 equipped with openings 6a, before being introduced into the liquid phase 2. After passage through the static mixer 3, the diffusion device 6 enables optimal diffusion of the mixture of HF and of HCO-1230za into the liquid phase 2. This optimal diffusion enables better regulation of the temperature of the liquid phase 2. Thus, according to a preferred embodiment, the reactor in which the present process is carried out may comprise a static mixer and at least one, preferably at least two, line(s) for supplying the streams A1 and A2. The static mixer 3 provides a homogeneous mixture to the diffusion device 6, enabling the diffusion of said streams A1 and A2 into said liquid phase 2. Thus, the reactor may also comprise a diffusion device equipped with openings and connected to said static mixer.

Figure 2:
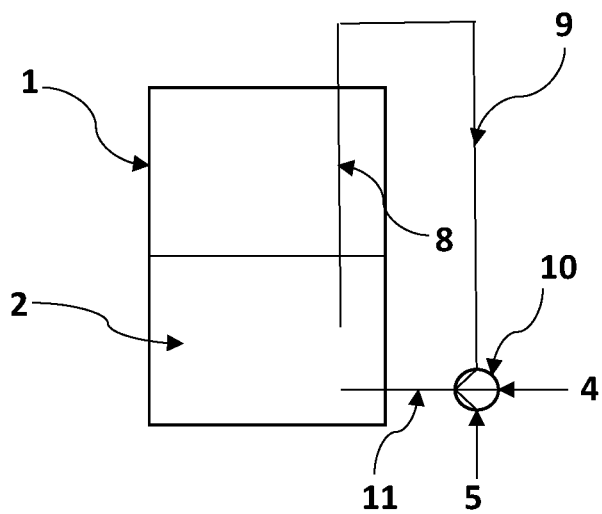
FIG. 2 schematically represents a reactor comprising, as stirring means, a device for recirculating the liquid phase, according to one embodiment of the present invention.

According to another embodiment, the reactor 1 comprises, as stirring means, a device for recirculating the liquid phase. This embodiment is illustrated in FIG. 2. In FIG. 2, the reactor 1 comprises a liquid phase 2 which is low in HF. The HF and the HCFO-1230za are introduced into the reactor via a respective supply line 4 or 5. The reactants, i.e. HF and HCFO-1230za, are introduced into the reactor 1 via a pump 10. The liquid phase 2 is extracted from the reactor 1 via the pipe 8 and is conveyed to the pump 10 via the pipe 9. The pump 10 makes it possible to introduce the liquid phase withdrawn via the pipes 8 and 9 into the liquid phase 2 of the reactor 1. This introduction is effected via a pipe 11 connecting the pump 10 to the reactor 1. Thus, according to a preferred embodiment, the reactor in which the present process is carried out may comprise at least one, preferably at least two, line(s) for supplying the streams A1 and A2.

The reactor may also comprise a pump capable of withdrawing a portion of said liquid phase contained in the reactor and of enabling the recirculation of said phase into the reactor. The reactor may also comprise pipes connecting said pump with the liquid phase of the reactor. Thus, the reactor may comprise at least one first pipe withdrawing the liquid phase from the reactor and conveying it to the pump, and at least one second pipe connecting the pump to the reactor and capable of introducing the withdrawn liquid phase into the reactor. Said lines for supplying the streams A1 and A2 may be connected to said pump. The reactor may also comprise at least one pipe withdrawing a gaseous stream from said reactor in order to convey it to said pump.

Figure 3:
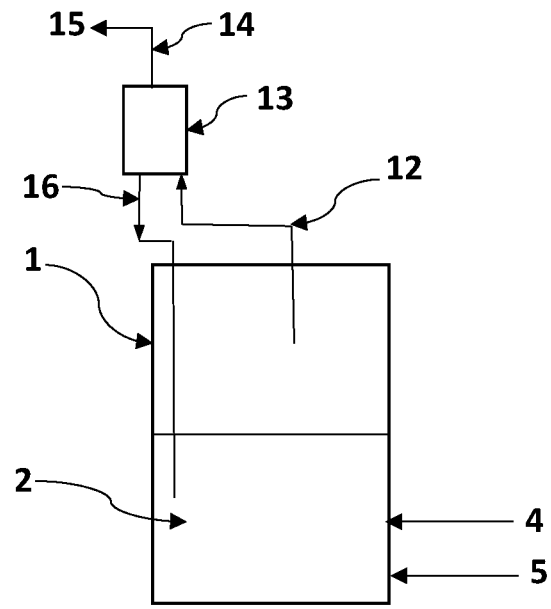
FIG. 3 schematically represents a reactor comprising, as stirring means, a device for returning a flow of HF into the liquid phase, according to one embodiment of the present invention.

According to another embodiment, the reactor 1 comprises, as stirring means, a device from returning a flow of HF into the liquid phase. This embodiment is illustrated in FIG. 3. In FIG. 3, the reactor 1 comprises a liquid phase 2 which is low in HF. The HF and the HCFO-1230za are introduced into the liquid phase 2 of the reactor 1 via a respective supply line 4 or 5. The gaseous phase present in the headspace of the reactor 1 (for example the stream C according to the present invention) is withdrawn therefrom via the pipe 12 in order to be conveyed to a distillation device 13. A stream 15 is recovered at the top of the distillation device 13 via the pipe 14. A stream 16 is recovered at the bottom of the distillation device 13 and is conveyed to the reactor 1 in order to be introduced into the liquid phase 2. Thus, according to a preferred embodiment, the reactor in which the present process is carried out may comprise at least one, preferably at least two, line(s) for supplying the streams A1 and A2. The reactor may also comprise a distillation device, at least one pipe feeding said distillation device with a gaseous phase originating from the headspace of said reactor. The distillation device also comprises a pipe connecting the bottom of the distillation device to the liquid phase of the reactor, said pipe making it possible to reintroduce a stream comprising HF into said liquid phase of the reactor. Said distillation device may also comprise a pipe connected at the top of said distillation device in order to withdraw a stream comprising 1-chloro-3,3,3-trifluoropropene.

Figure 4:
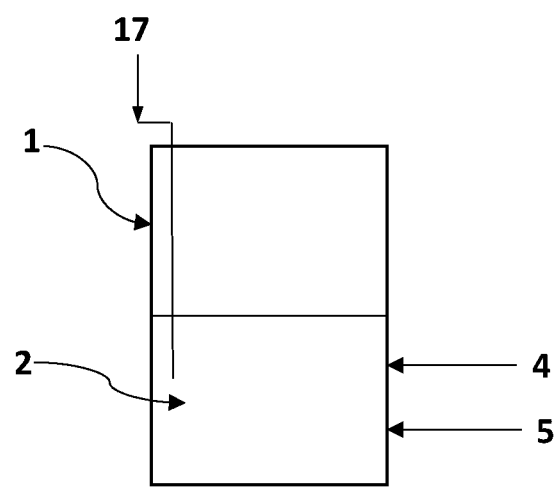
FIG. 4 schematically represents a reactor comprising, as stirring means, a device for injecting an inert gas, according to one embodiment of the present invention.

According to another embodiment, the reactor 1 comprises, as stirring means, a device for injecting an inert gas into the liquid phase. This embodiment is illustrated in FIG. 4. In FIG. 4, the reactor 1 comprises a liquid phase 2 which is low in HF. The HF and the HCFO-1230za are introduced into the reactor via a respective supply line 4 or 5. The inert gas is introduced into the liquid phase via a pipe 17. The inert gas may be nitrogen, argon or HCl. Thus, according to a preferred embodiment, the reactor in which the present process is carried out may comprise at least one, preferably at least two, line(s) for supplying the streams A1 and A2. The reactor may also comprise a pipe for supplying an inert gas which is immersed in said liquid phase contained in the reactor.

Figure 5:
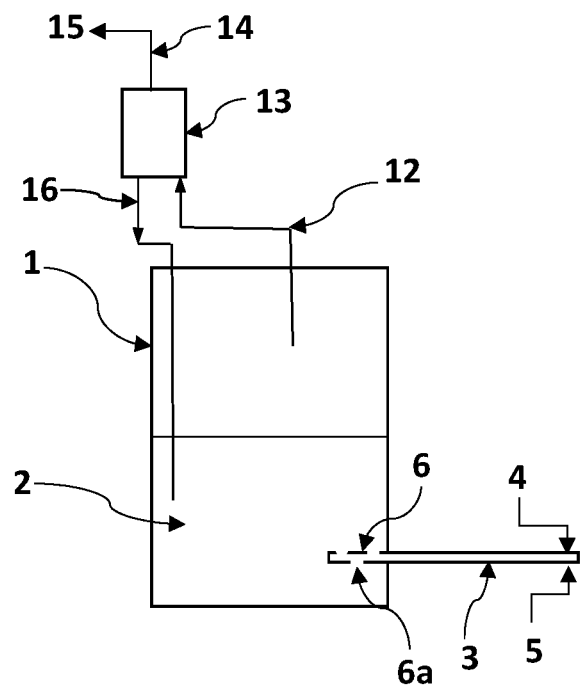
FIG. 5 schematically represents a reactor comprising, as stirring means, a static mixer and a device for returning a flow of HF into the liquid phase, according to one embodiment of the present invention.

According to another embodiment, the reactor 1 comprises, as stirring means, a static mixer and a device for returning a flow of the HF into the liquid phase. This embodiment is illustrated in FIG. 5. In FIG. 5, the reactor 1 comprises a liquid phase 2 which is low in HF. The HF and the HCFO-1230za are introduced into the liquid phase 2 of the reactor 1 from a respective supply line 4 or 5 feeding a static mixer 3, which is itself connected to a diffusion device 6 equipped with openings 6a. The gaseous phase present in the headspace of the reactor 1 (for example the stream C according to the present invention) is withdrawn therefrom via the pipe 12 in order to be conveyed to a distillation device 13. A stream 15 is recovered at the top of the distillation device 13 via the pipe 14. A stream 16 is recovered at the bottom of the distillation device 13 and is conveyed to the reactor 1 in order to be introduced into the liquid phase 2. Thus, according to a preferred embodiment, the reactor in which the present process is carried out may comprise at least one, preferably at least two, line(s) for supplying the streams A1 and A2, a static mixer and optionally a diffusion device equipped with openings. The static mixer makes it possible to homogenize the streams A1 and A2 and to diffuse them into said liquid phase with the aid, preferably, of the diffusion device equipped with openings. The reactor may also comprise a distillation device, at least one pipe feeding said distillation device with a gaseous phase originating from the headspace of said reactor. The distillation device also comprises a pipe connecting the bottom of the distillation device to the liquid phase of the reactor, said pipe making it possible to reintroduce a stream comprising HF into said liquid phase of the reactor. Said distillation device may also comprise a pipe connected at the top of said distillation device in order to withdraw a stream comprising 1-chloro-3,3,3-trifluoropropene.

Figure 6:
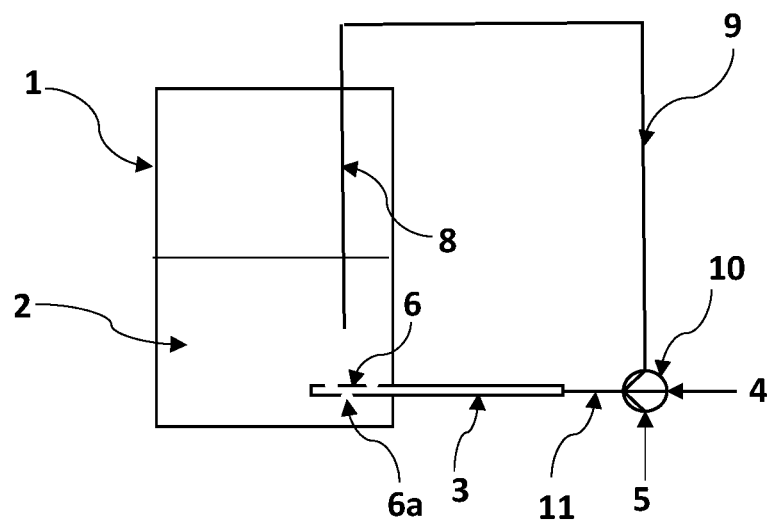
FIG. 6 schematically represents a reactor comprising, as stirring means, a static mixer and a device for recirculating the liquid phase, according to one embodiment of the present invention.

According to another embodiment, the reactor 1 comprises, as stirring means, a device for recirculating the liquid phase and a static mixer. This embodiment is illustrated in FIG. 6. In FIG. 6, the reactor 1 comprises a liquid phase 2 which is low in HF. The HF and the HCFO-1230za are introduced into the reactor from respective supply lines 4 and 5. The reactants, i.e. HF and HCFO-1230za, are introduced into the reactor 1 via a pump 10. The liquid phase 2 is extracted from the reactor 1 via the pipe 8 and is conveyed to the pump 10 via the pipe 9. The pump 10 makes it possible to introduce the liquid phase withdrawn via the pipes 8 and 9 into the liquid phase 2 of the reactor 1. The pipe 11 connects the pump 10 to the reactor 1 via the static mixer 3 and the diffusion device 6 equipped with openings 6a. A gaseous phase may also be present in the headspace of the reactor 1 (for example the stream C according to the present invention). Thus, according to a preferred embodiment, the reactor in which the present process is carried out may comprise at least one, preferably at least two, line(s) for supplying the streams A1 and A2. The reactor may also comprise a static mixer. The static mixer makes it possible to homogenize the streams A1 and A2 and to diffuse them into said liquid phase with the aid, preferably, of the diffusion device equipped with openings. The reactor may also comprise a pump capable of withdrawing a portion of said liquid phase contained in the reactor and of enabling the recirculation of said phase into the reactor. The reactor may also comprise pipes connecting said pump with the liquid phase of the reactor. Thus, the reactor may comprise at least one first pipe withdrawing the liquid phase from the reactor and conveying it to the pump, and at least one second pipe connecting the pump to said static mixer. Said lines for supplying the streams A1 and A2 may be connected to said pump.

Figure 7:
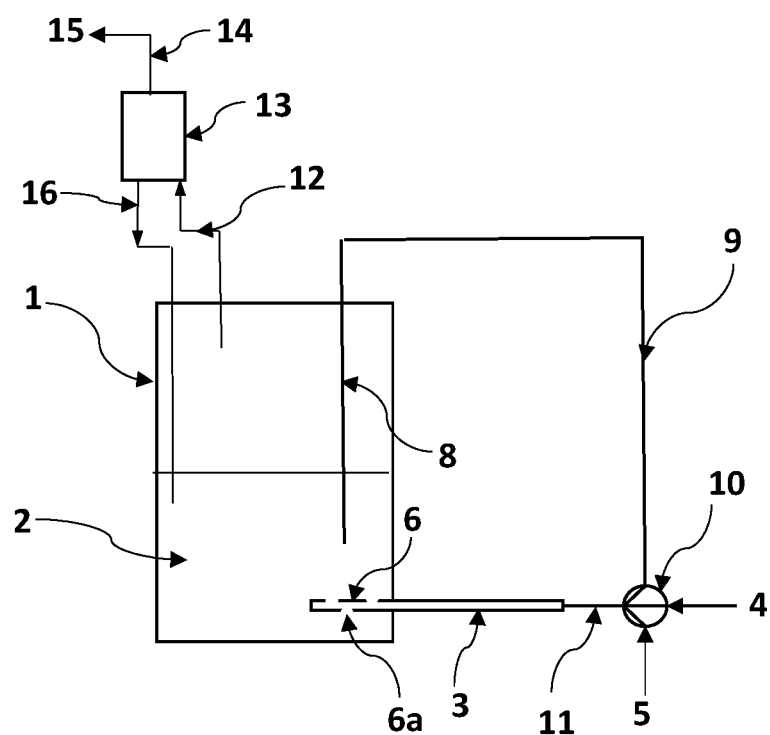
FIG. 7 schematically represents a reactor comprising, as stirring means, a static mixer, a device for returning a flow of HF into the liquid phase and a device for recirculating the liquid phase, according to one embodiment of the present invention.

According to another embodiment, the reactor 1 comprises, as stirring means, a device for recirculating the liquid phase, a static mixer and a device for returning a flow of the HF into the liquid phase. This embodiment is illustrated in FIG. 7. In FIG. 7, the reactor 1 comprises a liquid phase 2 which is low in HF. The HF and the HCFO-1230za are introduced into the reactor from respective supply lines 4 and 5. The reactants, i.e. HF and HCFO-1230za, are introduced into the reactor 1 via a pump 10. The liquid phase 2 is extracted from the reactor 1 via the pipe 8 and is conveyed to the pump 10 via the pipe 9. The pump 10 makes it possible to introduce the liquid phase withdrawn via the pipes 8 and 9 into the liquid phase 2 of the reactor 1. The pipe 11 connects the pump 10 to the reactor 1 via the static mixer 3 and the diffusion device 6 equipped with openings 6a. Part of the gaseous phase present in the headspace of the reactor 1 is withdrawn therefrom via the pipe 12 in order to be conveyed to a distillation device 13. A stream 15 is recovered at the top of the distillation device 13 via the pipe 14. A stream 16 is recovered at the bottom of the distillation device 13 and is conveyed to the reactor 1 in order to be introduced into the liquid phase 2. Thus, according to a preferred embodiment, the reactor in which the present process is carried out may comprise at least one, preferably at least two, line(s) for supplying the streams A1 and A2. The reactor may also comprise a static mixer. The static mixer makes it possible to homogenize the streams A1 and A2 and to diffuse them into said liquid phase with the aid, preferably, of the diffusion device equipped with openings. The reactor may also comprise a pump capable of withdrawing a portion of said liquid phase contained in the reactor and of enabling the recirculation of said phase into the reactor. The reactor may also comprise pipes connecting said pump with the liquid phase of the reactor. Thus, the reactor may comprise at least one first pipe withdrawing the liquid phase from the reactor and conveying it to the pump, and at least one second pipe connecting the pump to said static mixer. Said lines for supplying the streams A1 and A2 may be connected to said pump. The reactor may also comprise a distillation device, at least one pipe feeding said distillation device with a gaseous phase originating from the headspace of said reactor. The distillation device also comprises a pipe connecting the bottom of the distillation device to the liquid phase of the reactor, said pipe making it possible to reintroduce a stream comprising HF into said liquid phase of the reactor. Said distillation device may also comprise a pipe connected at the top of said distillation device in order to withdraw a stream comprising 1-chloro-3,3,3-trifluoropropene.

More particularly, the stirring means comprises a static mixer. Thus, the present process for producing 1-chloro-3,3,3-trifluoropropene (HCFO-1233zd), comprises the steps of:
i) providing:
  a stream A1 comprising HF,
  a stream A2 comprising 1,1,3,3-tetrachloropropene and/or 1,3,3,3-tetrachloropropene, and
  a reactor containing a liquid phase and comprising a static mixer,
i') contacting said stream A1 with said stream A2 in said static mixer to form a mixture B comprising HF, 1,1,3,3-tetrachloropropene and/or 1,3,3,3-tetrachloropropene,
ii') diffusing said mixture B into said liquid phase in order to carry out step ii) proceeding from this.

Thus, according to one particular embodiment, the present process for producing 1-chloro-3,3,3-trifluoropropene (HCFO-1233zd), comprises the steps of:
i) providing:
  a stream A1 comprising HF,
  a stream A2 comprising 1,1,3,3-tetrachloropropene and/or 1,3,3,3-tetrachloropropene, and
  a reactor containing a liquid phase and comprising a static mixer,
i') contacting said stream A1 with said stream A2 in said static mixer to form a mixture B comprising HF, 1,1,3,3-tetrachloropropene and/or 1,3,3,3-tetrachloropropene,
ii') diffusing said mixture B into said liquid phase,
ii) contacting, in said liquid phase, said stream A1 comprising HF with said stream A2 comprising 1,1,3,3-tetrachloropropene and/or 1,3,3,3-tetrachloropropene under conditions which are sufficient to produce a stream C comprising 1-chloro-3,3,3-trifluoropropene, HF and HCl,
iii) recovering said stream C.

The use of a static mixer enables optimal control of the temperature of the liquid phase during the implementation of step ii). Thus, in this embodiment, the temperature of said liquid phase is substantially constant. Preferably, the use of a static mixer allows a variation of the temperature of the liquid phase by a maximum of 0.5° C.

Preferably, the static mixer is combined with one or more stirring means as defined in the present application. Thus, the reactor may comprise, in addition to the static mixer, a device for returning a flow of the HF into the liquid phase and/or a device for recirculating said liquid phase as defined in the present application, in particular in FIGS. 5 to 7. Alternatively, the reactor may comprise, in addition to the static mixer, a device for injecting an inert gas into the liquid phase.

In addition, the static mixer makes it possible to initiate the fluorination reaction between the hydrofluoric acid and the 1,1,3,3-tetrachloropropene and/or 1,3,3,3-tetrachloropropene. In said mixture B, the HF is in gaseous form or liquid form. In said mixture B, the 1,1,3,3-tetrachloropropene and/or 1,3,3,3-tetrachloropropene is in liquid form. Said mixture B may also comprise compounds having a degree of fluorination greater than that of 1,1,3,3-tetrachloropropene or 1,3,3,3-tetrachloropropene. The degree of fluorination corresponds to the number of fluorine atoms contained in the compound considered. For example, the mixture B may comprise trichlorofluoropropene (HCFO-1231) or dichlorodifluoropropene (HCFO-1232) compounds. It has thus been discovered, surprisingly, that the use of starting products such as 1,1,3,3-tetrachloropropene and/or 1,3,3,3-tetrachloropropene made it possible to produce 1-chloro-3,3,3-trifluoropropene more easily and more rapidly under operating conditions which are less constraining in terms of temperature and pressure. Thus, the use of starting products such as 1,1,3,3-tetrachloropropene and/or 1,3,3,3-tetrachloropropene in combination with the static mixer makes it possible to initiate the fluorination reaction as soon as they are put in contact in said static mixer. The HCl byproduct generated during initiation of the reaction contributes to the homogeneity of the mixture of starting materials. Thus, the implementation of the process is more efficient than with a starting product such as 1,1,1,3,3-pentachloropropane (HCC-240fa). The static mixer makes it possible in addition to control the diffusion of the mixture B into said liquid phase by limiting the formation of heavy compounds (as mentioned above).

The stream C is preferably in gaseous form. The stream C may also comprise organic compounds such as intermediates of the fluorination reaction or coproducts. Mention may in particular be made of dichlorodifluoropropene, trichloromonofluoropropene, fluorotetrachloropropane, pentafluoropropane, difluorotrichloropropane, dichlorotrifluoropropane and 1,3,3,3-tetrafluoropropene. Preferably, stream C comprises 1,3,3,3-tetrafluoropropene and 1,1,1,3,3-pentafluoropropane. The molar content of 1,3,3,3-tetrafluoropropene in said stream C is less than 0.2 mol %. The molar content of 1,1,1,3,3-pentafluoropropane in said stream C is less than 0.5 mol %.

According to a preferred embodiment, stream C is purified, preferably by distillation, to form a stream C1 comprising HCl and a stream C2 comprising 1-chloro-3,3,3-trifluoropropene and HF, said stream C2 itself being separated, for example by cold settling, into a stream C3 comprising 1-chloro-3,3,3-trifluoropropene and a stream C4 comprising HF recycled to step i') or ii). The cold settling step can be carried out at a temperature of −50° C. to 50° C., preferably of −30° C. to 0° C.

EXAMPLES

The examples that follow illustrate the invention without limiting it. The apparatus used consists of an autoclave having a capacity of 1 liter with a jacket, made of 316L stainless steel. It is provided with means for measuring temperature and pressure. Openings at the top of the autoclave allow the introduction of the reactants and the removal of the products. A condenser is provided at the top, as is a valve for regulating the pressure. The condenser is temperature controlled by means of a thermostatically controlled bath. Due to the pressure regulation, the reaction products are progressively extracted. Thus, the flow of outlet gas passes into a washing device which collects the hydracids HF and HCl, and is then cooled in liquid nitrogen. The molar distribution of the products of the outlet gas is analyzed periodically, by GC (gas chromatography). At the end of the test, the reaction medium is cooled to room temperature and depressurized.

Comparative Example 1: Liquid-Phase Fluorination of 1230za without Stirring

An amount of HF of 150 g is introduced into the autoclave. The temperature of the reactor is adjusted to 90° C. in the liquid phase. The pressure is regulated at 13 bara. Once the temperature has stabilized, 135 g of 1230za are introduced into the reactor. The molar ratio of HF to the organic compound is therefore 10. The temperature of the liquid phase taken at the same time at two points is different. After two hours of reaction, the test is stopped and processed in accordance with the methods described above. The conversion of HCO-1230za is 69.2%. The amount of heavy compounds formed is estimated by the mass of organic products (other than 1230za) recovered from the reactor at the end of reaction divided by the mass of 1230za which has reacted. This is 9% by weight.

Example 2: Liquid-Phase Fluorination of 1230za with Stirring

An amount of HF of 150 g is introduced into the autoclave. The reactor is equipped with a mechanical stirring means. The temperature of the reactor is adjusted to 90° C. in the liquid phase. The pressure is regulated at 13 bara. Once the temperature has stabilized, 136 g of 1230za are introduced into the reactor. The molar ratio of HF to the organic compound is therefore 10. The temperature of the liquid phase taken at the same time at two different points does not vary. After two hours of reaction, the test is stopped and processed in accordance with the methods described above. The conversion of HCO-1230za is 100%. The amount of heavy compounds formed is estimated by the mass of organic products (other than 1230za) recovered from the reactor at the end of reaction divided by the mass of 1230za which has reacted. This is 6% by weight.

The presence of a stirring means as provided by the present invention makes it possible to reduce the amount of heavy compounds formed during the fluorination reaction. As demonstrated by example 2, the presence of a stirring means makes it possible to reduce the content of heavy compounds to 6% by weight, compared to 9% in example 1 carried out in the absence of stirring.

Example 3: Liquid-Phase Fluorination of 1230za with a Static Mixer

The pilot apparatus used consists of a reactor with a capacity of 60 liters, made of 316L stainless steel. It is provided with means for measuring temperature, pressure, and liquid level. The two reactants are preheated. They are then mixed and fed into the reactor using a dip tube equipped with a static mixer and a diffuser at the end. An in-line withdrawal system allows the flow of outlet gas to be sampled, for which it is guided to a gas chromatograph. The reactants are fed in continuously, and the products are analyzed and collected continuously. An amount of 1230za of 25 liters is introduced into the reactor. The pressure regulation is adjusted to 15 bara. The reactants are then fed in at the following flow rates: 2.3 kg/h of HF and 3.2 kg/h of 1230za. The temperature of the liquid phase taken at the same time at five different points after 24 h of continuous operation of the reactor varies by a maximum of 0.5° C. The composition of the resulting gaseous organic flow is given: 95.4 mol % of HFCO-1233zdE, 4.17 mol % of HCFO-1233zdZ, 0.14 mol % of 1234ze (E+Z), 0.002 mol % of 245fa.

Example 4 (Comparative): Liquid-Phase Fluorination of 1230za without a Static Mixer Example 3 is reproduced without a static mixer. The two reactants are fed to the reactor independently using two dip tubes. The temperature of the liquid phase taken at the same time at five different points in the reactor varies between 89° C. at the liquid surface and 94° C. at the bottom of the reactor. The composition of the resulting gaseous organic flow is given: 94.6 mol % of HFCO-1233zdE, 4.53 mol % of HCFO-1233zdZ, 0.18 mol % of 1234ze (E+Z), 0.025 mol % of 245fa.

The presence of a static mixer as stirring means also makes it possible to reduce the content of coproducts. Specifically, the content of 1234ze and 245fa decreases when the fluorination process is carried out in the presence of a stirring means such as the static mixer.

The invention claimed is:
1. A process for producing 1-chloro-3,3,3-trifluoropropene (HCFO-1233zd), comprising the steps of:
   i) providing:
      a stream A1 comprising HF,
      a stream A2 comprising 1,1,3,3-tetrachloropropene and/or 1,3,3,3-tetrachloropropene, and
      a reactor containing a liquid phase,
   ii) in said reactor, contacting, in said liquid phase, said stream A1 comprising HF with said stream A2 comprising 1,1,3,3-tetrachloropropene and/or 1,3,3,3-tetrachloropropene under conditions which are sufficient to produce a stream C comprising 1-chloro-3,3,3-trifluoropropene, HF and HCl,
   iii) recovering said stream C,
   wherein said reactor is provided with means for stirring said liquid phase so as to keep the temperature of said liquid phase substantially constant during step ii) and wherein said liquid phase in step ii) comprises less than 15% by weight of HF.

2. The process as claimed in claim 1, wherein during the implementation of step ii), the temperature of said liquid phase varies by a maximum of 2° C.

3. The process as claimed in claim 1, wherein said stirring means comprise a static mixer, a device for injecting an inert gas into said liquid phase, a device for recirculating the liquid phase, or a device for returning a flow of HF into said liquid phase.

4. The process as claimed in claim 1, wherein the stirring means comprises a static mixer and the process comprises the steps of:
  i) providing:
    the stream A1 comprising HF,
    the stream A2 comprising 1,1,3,3-tetrachloropropene and/or 1,3,3,3-tetrachloropropene, and
    the reactor containing the liquid phase and comprising the static mixer,
  i') contacting said stream A1 with said stream A2 in said static mixer to form a mixture B comprising HF, 1,1,3,3-tetrachloropropene and/or 1,3,3,3-tetrachloropropene,
  ii') diffusing said mixture B into said liquid phase in order to carry out step ii) proceeding from this.

5. The process as claimed in claim 1, wherein said stream A1 and said stream A2 are preheated before carrying out step ii).

6. The process as claimed in claim 1, wherein step ii) is carried out at a temperature of between 20° C. and 150° C.

7. The process as claimed in claim 1, wherein step ii) is carried out at a pressure of between 1 and 20 bara.

8. The process as claimed in claim 1, wherein it is carried out in continuous mode in a single reactor.

9. The process as claimed in claim 1, wherein step ii) is carried out in the absence of catalyst.

10. The process as claimed in claim 1, wherein stream C is purified—to form a stream C1 comprising HCl and a stream C2 comprising 1-chloro-3,3,3-trifluoropropene and HF, said stream C2 itself being separated into a stream C3 comprising 1-chloro-3,3,3-trifluoropropene and a stream C4 predominantly comprising the HF recycled to step i') or ii).

11. The process as claimed in claim 1, wherein said liquid phase in step ii) comprises less than 10% by weight of HF.

12. The process as claimed in claim 1, wherein stream C is a gaseous stream.

13. The process as claimed in claim 1, wherein said liquid phase in step ii) comprises less than 6% by weight of HF.

14. The process as claimed in claim 1, wherein said liquid phase in step ii) comprises less than 8% by weight of HF.

15. The process as claimed in claim 4, wherein said stream A1 and said stream A2 are preheated before carrying out step i').

* * * * *